United States Patent [19]

Borish

[11] Patent Number: 5,165,427
[45] Date of Patent: Nov. 24, 1992

[54] CYSTEINAMIDE—CONTAINING PERMANENT WAVE COMPOSITION AND METHOD

[75] Inventor: Edward T. Borish, Mahwah, N.J.
[73] Assignee: Helene Curtis, Inc., Chicago, Ill.
[21] Appl. No.: 730,666
[22] Filed: Jul. 16, 1991
[51] Int. Cl.$^5$ ............................................. A45D 7/04
[52] U.S. Cl. ................................. 132/204; 132/203; 424/70; 424/71
[58] Field of Search ............... 132/202, 203, 204, 205, 132/210; 424/70, 71

[56] References Cited

U.S. PATENT DOCUMENTS 4,273,143  6/1981  Klemm ................. 132/204
4,301,820  11/1981  Cannell et al. .............. 132/204

Primary Examiner—Gene Mancene
Assistant Examiner—Frank A. LaViola
Attorney, Agent, or Firm—Marshall, O'Toole, Gerstein, Murray & Bicknell

[57] ABSTRACT

A new and improved cysteinamide reducing agent, such as cysteinamide hydrochloride, capable of breaking sulfur to sulfur cystine bonds in human hair for use in permanent wave and hair straightening compositions, to provide additional set retention in hair sprays, styling aids, mousse and hair bodifying compositions, and to provide the hair with additional body when incorporated into shampoos, conditioners and conditioning shampoo compositions. In one embodiment, the cysteinamide reducing agent compounds are used for the reducing agent in permanent waving of human hair in the form of a mild alkaline permanent wave reducing composition and in a method of permanently waving or reshaping human hair that provides a strong, long lasting curl.

13 Claims, No Drawings

CYSTEINAMIDE—CONTAINING PERMANENT WAVE COMPOSITION AND METHOD

FIELD OF THE INVENTION

The present invention is directed to a cysteinamide-containing composition and method for providing set retention to human hair, such as in a styling aid, hair bodifying composition hair spray, mousse, shampoo, conditioner, conditioning shampoos, and particularly in a reducing agent composition for relatively permanently reshaping or curling human hair into a lasting curl pattern. More particularly, the present invention is directed to a composition and method capable of forming a "permanent" wave in human hair such that regardless of the condition of the hair, i.e., whether it be substantially undamaged or normal hair, tinted hair, frosted hair, bleached hair or hair substantially damaged as a result of some other prior hair treatment or environmental condition, the composition will permanently reshape both normal and damaged hair to substantially the same extent. The composition can be applied to the hair as a single composition formula applied to both normal and damaged hair for the same period of time, with or without heating, to produce a strong curl like that of an alkaline permanent wave composition while leaving the hair feeling soft like an acid permanent wave composition.

BACKGROUND OF THE INVENTION AND PRIOR ART

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound onto a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

There are three general types of permanent wave compositions or lotions used to break the cystine bonds in human hair, generally known as acid wave compositions; alkaline wave compositions; and neutral wave compositions. Of these three, the acid and alkaline wave compositions are most significant commercially. Permanent wave compositions containing an alkaline salt of thioglycolic acid (TG), such as ammonium thioglycolate as the reduction agent, are generally known as alkaline wave compositions and generally have a pH in the range of about 7.5 to about 9.4. The alkaline wave compositions are known as the conventional cold wave compositions, since free alkali penetrates and swells the hair shaft allowing the reducing agent to enter the hair shaft and break the sulfur to sulfur bonds without added heat. The permanent wave compositions containing glycerol monothioglycolate (GMTG) are known as acid wave compositions even though the pH of these compositions can be as high as about 9.0. Generally speaking, the acid permanent wave compositions have a lower pH than the alkaline permanent wave compositions and, therefore, require heat and/or longer processing time to achieve sufficient reaction of the reducing agent. The alkaline permanent wave compositions produce a stronger, longer lasting curl while the acid permanent wave compositions provide a softer feel but a less distinct curl pattern of shorter curl duration.

The reducing agents most commonly used in cold waving hair lotions for rupturing cystine linkages are thiols or mercaptans as well as sulfites and/or bisulfites. A number of mercaptans can only provide acceptable efficiency at high pH whereas others with a lower pK and a high ionization constant can be effective at lower pH levels. For example, the ammonium salt of thioglycolic acid can provide acceptable waving efficiency (reduction) if the pH of the solution exceeds 9. Other compounds such as thioglycolamides or glycol thioglycolates, sulfites and/or bisulfites can be used at neutral or even slightly acidic pH. The following are mercaptans and thiois which have commonly been used in cold waving lotions: thioglycolic acid, thiolactic acid, cysteine, thioglycerol, thioglycolic hydrazide, thioglycolamide, glycerol monothioglycolate, beta-mercapto-propionic acid, N-hydroxyethyl mercaptoacetamide, N-methyl mercapto-acetamide, beta-mercaptoethylamine, beta-mercapto-propionamide, 1-mercaptoethanesulfonic acid, dimercapto-adipic acid, dithiothreitol, homocysteinethiolactone, cysteine derivatives, and polythiol derivatives formed by the addition of cysteamine onto a maleic anydride-alkylvinylether copolymer. The sulfites and/or bisulfites most commonly used are the sodium and ammonium salts. The amount of the reducing agent used is that sufficient to rupture a sufficient number of disulfide bonds for effective hair waving or hair straightening as would be appreciated by one of ordinary skill in the art, for example about 0.1% to about 22% by weight of the composition, preferably about 1.0% to about 22% by weight.

The reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate anion) form at a pH near neutral, or slightly acidic pH. Hence, the pKa value shows that some mercaptans are efficient at high pH while others with a low pKa value and high ionization constant are efficient at lower pH values. For example, it is well known that the alkaline salts of thioglycolic acid, e.g., the ammonium salt of thioglycolic acid (pKa=10.4) has acceptable waving efficiency only if the pH of solution exceeds 9, see Zviak, Charles, The Science of Hair Care, Permanent Waving and Hair Straightening, p. 191, 1986; while amides such as thioglycolamide (pKa=8.4), and esters such as glycerol thioglycolate (pKa=7.8) give acceptable waving efficiency at neutral and even slightly acid pH.

The cysteinamide reducing agent of the composition and method of the present invention is unexpectedly effective in the pH range of about 7.5 to about 9.5 and particularly in the pH range of about 8.0 to about 9.2.

Different reducing agents are effective to break the cystine bonds that cross-link human hair protein at different pHs. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pH's in the range of about 7.5 to 9.5, require an alkaline salt of thioglycolic acid or an alkaline salt of a dithioglycolic acid - so that the alkali can penetrate and swell the hair shaft for easier penetration of the reducing agent in order to break the sulfur to sulfur cystine bonds.

When the reducing agent is a salt of thioglycolic acid, such as ammonium thioglycolate, the reducing agent breaks the sulfur to sulfur cystine hair bonds best under high pH conditions (above 9.0) and therefore is included in a lotion in an amount sufficient to provide enough free alkali in solution for a composition pH of about 7.5 to 9.5. Alternatively, the high pH can be provided with a different alkali in the reducing agent composition, such a monoethanolamine, disopropanolamine or metal hydroxides. The lotion can be buffered, such as with ammonium bicarbonate or other known buffers, to maintain a suitable pH.

The use of diammonium dithiodiglycolate in acid or alkaline permanent wave lotions allows greater flexibility in processing time because it minimizes the possibility of overprocessing. This is due to the fact that the reaction of thioglycolic acid (TGA) with hair keratin is an equilibrium process. Thus by including diammonium dithiodiglycolate (oxidized TGA) in the wave lotion, the rate of the reaction of the thioglycolic acid with hair keratin is decreased and prevented from going to completion.

Generally, the permanent wave compositions of the prior art do not include moisturizers, such as glycerine, since moisturizers cause loss of curl, as disclosed in Cannell et al. U.S. Pat. No. 4,301,820.

One of the biggest problems associated with the permanent waving process is due to human error in the person applying the permanent waving lotion. If the reducing agent is applied to the hair shaft for the wrong period of time, too many or too few of the sulfur to sulfur bonds in the hair shaft are broken, resulting in seriously damaged hair or resulting in hair which has not been sufficiently treated to achieve a permanent wave with long lasting potential. Some of the reasons that the person applying the permanent wave composition has difficulty in determining the correct amount of time for processing is that the reducing agent reaction in breaking the sulfur to sulfur bonds is dependent upon the amount of heat applied to the hair; the amount of time the reducing agent is in contact with the hair; the concentration of reducing agent; the pH of the lotion applied; and the condition of hair.

Perhaps the most difficult factor for the applier of the permanent wave lotion to assess in determining how long to apply the reducing agent to the hair is the condition of the hair at the time of the permanent wave. It is well documented in the literature and prior art that the hair can be damaged by abuse of chemicals, e.g., by shampooing, permanent waving, tinting, frosting, bleaching, and particularly any hair treatment involving the use of hydrogen peroxide; mechanical treatment, e.g., thermal appliances; and environmental conditions, e.g., climate and pollution. It is well known that damaged hair, depending upon the stage and degree of damage of the hair, has significantly different chemical activity to reducing agents than normal or undamaged hair. If too many or the sulfur to sulfur bonds in the hair are broken by the reducing agent, the hair will be seriously weakened and may disintegrate.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, and capable of retaining this shape. If too few of the sulfur to sulfur bonds are broken, the natural or normal configuration of the hair will predominate, causing the hair to retain its previous shape. This is because the predominant, prior or natural, bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be stronger than the prior or natural cystine hair bonds. It is desired, therefore, when permanent waving, that enough new bonds in a new hair configuration are formed during permanent waving to outweigh the number of old bonds remaining that tend to form the hair in its prior of natural configuration, whether it be straight or naturally curled.

Since damaged hair already has a significant number of the sulfur to sulfur cystine bonds broken due to some chemical, mechanical or environmental abuse, particularly the chemical abuses, such as bleaching, tinting or frosting, it is difficult to determine what length of time, and what reducing agent concentration to apply to the hair to provide the hair with the proper number of sulfur to sulfur bonds remaining after the reducing agent treatment. Significantly damaged hair, such as tinted hair, may require a reducing agent lotion application for a period of only about 5 minutes whereas a normal hair, not significantly damaged, may require the reducing agent lotion for a period of approximately 20 minutes under the same reducing agent concentration and temperature in order to result in both the damaged and normal hair having approximately the same curl configuration. Ideally, after the reducing agent treatment, every one of the hair shafts treated will contain the same ratio of broken to unbroken bonds so that this same ratio can be re-established in each hair shaft when the hair is in the new configuration to provide a consistent strong curl over the entire head of hair.

Generally, the reducing agent lotion is applied to the hair by first shampooing the hair and then applying the reducing agent lotion to the hair, either before or after the hair is wrapped around suitable rollers. Since it is not possible for even the experienced permanent wave applier to accurately determine visually the extent of damage to the hair in order to have a better idea of how long the reducing agent should be in contact with the hair, it is necessary to take a "test curl" so that after a predetermined amount of time, for example 10 minutes, a first roller is removed from the hair and the curl is felt and stretched in an attempt to determine if the curl formation is strong enough. Once it is determined that the reducing agent has been in contact with the hair for a sufficient time period, the hair is rinsed thoroughly with water while still on the rollers or rods and, while the hair remains on the rollers or rods, a neutralizing agent is applied to oxidize and reform the sulfur to sulfur bonds while the hair is in the new, rolled configuration. The neutralizing agent contains an oxidizing agent, such as hydrogen peroxide or a bromate salt, in order to reestablish the sulfur to sulfur bonds to leave the hair in a relatively permanent, e g., 2-4 months, new configuration. The rods are removed, before or after rinsing out the neutralizing agent.

When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

Prior art patents directed to permanent waving compositions intended to permanently wave both normal and damaged hair are found in the Klemm et al U.S. Pat. No. 4,273,143; and Cannell et al U.S. Pat. No. 4,301,820. Japanese Patent No. 57-212110 appears to be directed to a post-permanent treatment containing glycerine to give hair sheen and luster.

In accordance with the present invention, a new cysteinamide reducing agent has been found for breaking sulfur to sulfur cystine bonds in hair that is unexpectedly effective as a reducing agent to break cystine hair bonds in the permanent waving process and can provide set retention benefits and other bodifying advantages in hair sprays, styling aids, mousse compositions, shampoos, conditioners, conditioning shampoos, hair bodifying compositions, and hair straightening compositions. In accordance with one important embodiment of the present invention, the cysteinamide reducing agent is included in an alkaline permanent wave composition in a single formula that can be applied in a single predetermined amount of time to the hair, regardless of the structure of the hair, whether it be damaged or not, and this compositions is capable of being water wrapped without the use of a dryer, hair caps or other heat treatment to speed the reducing agent reaction. The composition of the present invention produces a strong curl like an alkaline wave composition yet leaves the hair feeling soft like an acid wave composition.

SUMMARY OF THE INVENTION

In brief, the present invention is directed to a new and improved reducing agent capable of breaking sulfur to sulfur cystine bonds in human hair for use in permanent wave and hair straightening compositions, to provide additional set retention in hair sprays, styling aids, mousse and hair bodifying compositions, and to provide the hair with additional body when incorporated into shampoos, conditioners and conditioning shampoo compositions. In accordance with one important embodiment of the present invention, the cysteinamide reducing agent compounds of the present invention are used for the reducing agent in permanent waving of human hair in the form of a mild alkaline permanent wave reducing composition and in a method of permanently waving or re-shaping human hair that provides a strong, long lasting curl like an alkaline permanent wave composition but leaves the hair soft like an acid permanent wave composition while minimizing further damage to already damaged hair. The composition used as a reducing agent in the permanent waving of human hair contains a cysteinamide, such as cysteinamide hydrochloride,

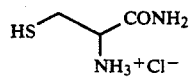

in an amount of about 1% to about 22% by weight, and, optionally, a hair softening and/or moisturizing agent, such as glycerine, in an amount of about 0.1% to about 20% by weight, preferably about 0.1% to about 15% by weight; and sufficient additional alkali, if necessary, to bring the pH of the composition up to about 7.5 to about 9.5. This reducing agent composition is easy to use and apply without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness.

The cysteinamide reducing agent can be used in conjunction with any oxidizing agent composition (neutralizer) to re-set the hair in a desired configuration. Any neutralizing composition can be applied to the waved or straightened hair after the cysteinamide reducing agent to restore the disulfide linkages in the hair keratin, and contain in aqueous solution any of the oxidizing agents conventionally employed for this purpose, in conventional amounts, such as hydrogen peroxide, urea hydrogen peroxide, sodium carbonate peroxide, sodium or potassium bromate, sodium perborate, or sodium hypochlorite.

Accordingly, an aspect of the present invention is to provide a new and improved cysteinamidecontaining permanent wave composition capable or breaking sulfur to sulfur bonds in human hair so that the hair can be reconfigured in a different configuration. The sulfur to sulfur human hair bonds can be reestablished with any oxidizing agent to maintain the new hair configuration for a substantial time period.

Another aspect of the present invention is to provide a new and improved permanent wave lotion containing a cysteinamide reducing agent capable of breaking sulfur to sulfur hair bonds.

Another aspect of the present invention is to provide a new and improved permanent wave lotion composition capable of breaking sulfur to sulfur human hair bonds significantly better than cysteine.

Another aspect of the present invention is to provide an aqueous composition containing cysteinamide for reducing human hair to provide additional set retention and body in hair sprays, mousse bodifying compositions, shampoos, conditioners, conditioning shampoos, and other personal hair care compositions.

These and other aspects and advantages of the present invention will become apparent from the following detailed description of the preferred embodiments.

DETAILED DESCRIPTION OF THE PREFERRED EMBODIMENT

The present invention is directed to hair care compositions that include a cysteinamide reducing agent capable of providing the hair with increased set retention and body that is useful in hair sprays, hair bodifying compositions, mousse compositions, hair conditioning compositions, shampoos, and conditioning shampoos, and particularly for use as a reducing agent in permanently waving hair.

The compositions of the present invention containing a cysteinamide reducing agent, in the form of a permanent wave reducing composition, provide a mild alkaline permanent wave and are capable of waving or reshaping human hair to provide a strong, long lasting curl, or straightening effect, like an alkaline permanent wave composition while leaving the hair soft like an acid permanent wave composition without further damaging already damaged hair. Generally, the composition contains a cysteinamide reducing agent, such as cysteinamide hydrochloride, in an amount of about 1% by about 22% by weight, particularly about 4% to about 16% by weight; and, optionally, a hair moisturizer and/or softener, for example, selected from a polyhydroxyl alkyl compound, a polyalkylene glycol glycerol ether, an ethoxylated fatty alcohol, a fatty alcohol polymerized ether, and mixtures thereof in an amount of about 0.0% to about 20% by weight, particularly about 0.1% to about 15% by weight.

Optionally, the composition of the present invention includes a conditioner to improve the combing and manageability of the hair. Particularly, suitable conditioners are the polymeric quaternary ammonium salts, such as Polyquaternium 1 through Polyquaternium 14, inclusive, conditioners defined on page 245, CTFA Cosmetic Ingredient Dictionary, Third Edition, 1982, hereby incorporated by reference. The following examples of water-soluble quaternary ammonium compounds are also useful as water-soluble quaternary ammonium compounds that can be used in the method and composition of the present invention:

| | |
|---|---|
| Lauryltrimethylammonium chloride | (Laurtrimonium chloride); |
| Stearyltri (2-hydroxyethyl) ammonium chloride | (Quaternium-16); |
| Lauryldimethylbenzyl-ammonium chloride | (Lauralkonium chloride); |
| Oleyldimethylbenzyl-ammonium chloride | (Olealkonium chloride); |
| Dilauryldimethylammonium chloride | (Dilauryldimonium chloride); |
| Cetyldimethylbenzylam-monium chloride | (Cetalkonium chloride); |
| Dicetyldimethylammonium chloride | (Dicetyldimonium chloride); |
| Laurylpyridinium chloride | (Laurylpyridinium chloride); |
| Cetylpyridinium chloride | (Cetylpyridinium chloride); |
| N-(soya alkyl)-N,N,N-trimethyl ammonium chloride | (Soyatrimonium chloride); |
| Polydiallyldimethyl-ammonium chloride | (Polyquaternium-6); |
| Diallyldimethyl ammonium salt copolymerized with acrylamide | (Polyquaternium-7); |
| Guarhydroxypropyltri-monium chloride | (Guarhydroxypropyltrimonium chloride); |
| Copolymer of N-vinyl-pyrrolidone and N,N-dimethylaminoethyl-methacrylate, quaternized with dimethyl-sulfate | (Polyquaternium-11); |
| Copolymer of acrylamide and N,N-dimethylamino-ethyl methacrylate, quaternized with di-methyl sulfate | (Polyquaternium-5); |
| Cationic hydroxyethyl-cellulosics | (Polyquaternium-10); |
| Cetionic hydroxyethyl-cellulosics | (Polyquaternium-24); |
| Cetyltrimethylammonium chloride | (Cetrimonium chloride); |
| Decyldimethyloctyl-ammonium chloride | (Quaternium-24); |
| Myristyltrimethyl-ammonium chloride | (Mytrimonium chloride); |
| Polyoxyethylene (2)-cocomonium chloride | (PEG-2 Cocomonium chloride); |
| Methylbis (2-hydroxy-ethyl) cocoammonium chloride | (PEG-2 Cocoyl Quaternium-4); |
| Methylpolyoxyethylene-(15) cocoammonium chloride | (PEG-15 Cocoyl Quaternium-4); |
| Mythylbis (2-hydroxy-ethyl) octadecyl ammonium chloride | (PEG-2 Stearyl Quaternium-4); |
| Methylpolyoxyethylene-(15) octadecylammonium chloride | (PEG-15 Stearyl Quaternium-4); |
| Methylbis (2-hydroxyethyl)-oleylammonium chloride | (PEG-2 Oleyl Quaternium-4); |
| Methylpolyoxyethylene-(15) oleylammonium chloride | (PEG-15 Oleyl quaternium-4); | wherein the name in parenthesis is the compound name given by the Cosmetic, Toiletry and Fragrance Association, Inc. in the *CTFA Cosmetic Ingredient Dictionary*, 3rd ed., 1982, hereinafter referred to as the CTFA. The long chain radicals can be of only one carbon chain length or, usually are a mixture of carbon chain lengths derived from materials such as tallow, coconut oil, soya oil and the like, or from synthetically produced mixtures. Examples of watersoluble quaternary ammonium compounds having mixed carbon chain lengths include N-(soyaalkyl)-N,N,N-trimethyl ammonium chloride (soyatrimonium chloride) and polyoxyethylene (2) cocomonium chloride (PEG-2 cocomonium chloride). The conditioner, when added, is included in an amount of about 0.01% to about 2.0% by weight of the composition.

Other common cosmetic additives can be incorporated into the composition of the present invention, as long as the basic improved properties of retention, bodifying and/or permanent waving are not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols such as ethanol and isopropanol and mixtures. These solvents can be present in the hair setting composition of the present invention in an amount from about 1% to about 75% by weight and in particular from about 5% to about 50% by weight, based on the total weight of the composition.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners such as bentonite. These thickeners, when included, preferably are present in an amount from about 0.1% to about 10% by weight and, in particular, from about 0.5% to about 3% by weight, based on the total weight of the composition.

The permanent wave composition of the present invention has a pH in the range of about 7.5 to about 9.5. To achieve the full advantage of the present invention, the permanent wave composition has a pH of about 8.0 to about 9.2 for best curl retention when cold waved. This pH can be achieved by the addition of an alkanolamine, ammonia, an ammonium carbonate, or a metal hydroxide to the composition of the present invention.

The use of polyhydric alcohols or polyhydroxy alkane compounds, such as ethylene glycol, glycerine, propylene glycol, or polyoxyethylene glyceryl ether in the cysteinamide-containing compositions of the present invention leaves the hair in better condition due to humectant properties and surprisingly does not compromise curl formation, but provides the hair with a more uniform and natural curl.

Suitable moisturizers that can be included in the cysteinamide-containing aqueous compositions of the present invention include polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula

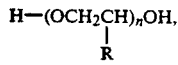

wherein R is H or CH3, and n has an average value of 2 to 600; when R=H, particularly suitable moisturizers have n in the range of 4 to 600; and when R=CH3, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether. Furthermore, the ethoxylated nonyl phenols and ethoxylated octyl phenols, particularly nonoxynol, $C_9H_{19}C_6H_4(OCH_2CH_2)_n$—OH, wherein n averages at least 6 and up to about 100; and octoxynol, $C_8H_{17}S_6H_4(OCH_2CH_2)_n$—OH, wherein n averages at least 7 and up to about 40, also are suitable moisturizers for use in the composition of the present invention. Suitable ethoxylated fatty alcohols for use as moisturizers in the composition of the present invention include compounds having the formula

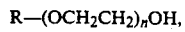

wherein R is an alkyl group containing from about 12 to about 30 carbon atoms and n averages at least 6. In addition, fatty alcohol polyglycol ethers having the formula

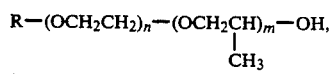

wherein R is an alkyl group containing from about 8 to about 18 carbon atoms, n=0 to 6, m=0 to 6, and n+m is at least 6, also are useful as moisturizers in the composition of the present invention.

The cysteinamide-containing permanent wave compositions of the present invention are easy to use and apply without damaging the hair while providing a strong, tight curl and leaving the hair unexpectedly soft. The composition can be lotion or water wrapped and can be used with or without heat. The compositions can be applied to any type of hair, regardless of structural damage to the hair, resulting in approximately the same degree of curl tightness and softness.

SYNTHESIS OF CYSTEINAMIDES

Cysteinamide was prepared in accordance with the method disclosed in the publication E. R. Atkinson, et al., *J. Med. Chem.* 1965, Vol. 8, p. 29, and depicted below in equation (1):

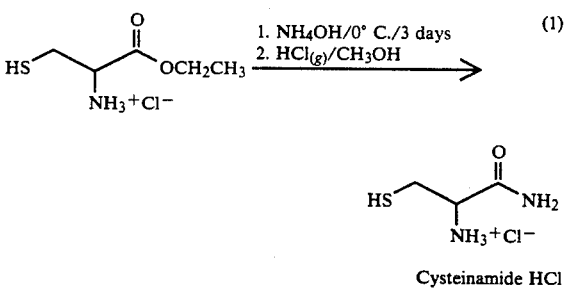

Cysteinamide HCl

A solution of L-cyteine ethyl ester hydrochloride (24 g, 0.129 mole) in 100 mL of ammonium hydroxide (28-30% ammonia content) was stored at 0° C for three days. The reaction mixture then was concentrated under reduced pressure and provided a solid white residue. The residue was dissolved in methanol, and the methanol solution was adjusted to pH 2 by the addition of a methanolic hydrogen chloride solution. The resulting solution Was stored at room temperature for 4 hours. A white crystalline product formed and then was filtered from the methanol and dried in a vacuum desiccator for 24 hours.

The white crystalline product (13 g) was recrystallized from a 1% sulfurous acid/ethanol solution to yield 11 g (54%) of cysteinamide as a white crystalline solid. The cysteinamide was dried in a vacuum desiccator for 24 hours to provide a product having the following properties: mp 186-188° C., TLC $R_f$ 0.45 (n-butanol/acetic acid/water/methanol, 10:5:5:1) detected with ninhydrin spray, IR 3450 cm$^{-1}$ (s), 3270 cm$^{-1}$ (s), 3500-2400 cm$^{-1}$ (br), 1730 cm$^{-1}$ (s), 1480 cm$^{-1}$ (s), MS CI (CH$_4$) m/z 121, NMR (d$_6$-DMSO) & 8.8-8.0 (br s, 3H), 8.3 and 8.1 (s, 1H), 7.7 and 7.6 (s, 1H), 4.1 and 4.0 (m, 1H), 3.4 and 3.1 (m, 3H), Analysis (Calculated): C, 23.01; H, 5.79; N, 17.89; S, 20.47. Analysis (Found): C, 23.26; H, 5.64; N, 17.98; S, 20.66.

The effectiveness of the cysteinamide reducing agents for permanent waving of human hair was compared to the use of cystine and, unexpectedly, as shown in Table I, cysteinamide was found to be about 50% more effective than cysteine in providing a strong tight curl.

TABLE I

| Waving of Hair with Cysteine vs Cysteinamide | |
| --- | --- |
| Treatment[a] | WE, %[b] |
| Cysteinamide (1 mL) | 27 |
| Cysteinamide (2 mL) | 30 |
| Cysteine (1 mL) | 17 |
| Cysteine (2 mL) | 20 |

[a]Wave lotions are 7.0% active in cysteinamide or cystein and pH 9.0 adjusted with ammonia. Processing was for 20 minutes at room temperature using tresses 150 mm in length and weight ca 1 g followed by neutralization for 5 minutes with a 2.0% solution of hydrogen peroxide.

[b]WE (Waving Efficiency) = $100 \times \left(1 - \frac{\text{Tress length after waving}}{\text{Initial tress length}}\right)$ Obviously, many modifications and variations of the invention as hereinbefore set forth can be made without departing from the spirit and scope thereof and therefore only such limitations should be imposed as are indicated by the appended claims.

What is claimed is:

1. A composition capable of breaking sulfur to sulfur bonds in human hair when in contact with said human hair so that said hair can be reconfigured in a predetermined configuration, comprising an aqueous solution of a cysteinamide in an amount of about .1% to about 22% by weight; and sufficient alkali such that the composition has a pH of about 7.5 to about 9.5.

2. The composition of claim 1 further including a polyhydric moisturizer selected from the group consisting of polyhydroxyalkyl compounds; polyalkylene glycols; glyceryl ether compounds; ethoxylated fatty alcohols; ethoxylated alkyl phenols; fatty alcohol polyglycol ether compounds; and mixtures thereof.

3. The composition of claim 1, wherein the cysteinamide is included in an amount of about 4% to about 16% by weight of the composition.

4. The composition of claim 3, wherein the cysteinamide is cysteinamide hydrochloride.

5. The composition of claim 2, wherein the moisturizer is glycerine or a polyalkylene glycol ether of glycerine having an average ethoxylation value of 5 to 50.

6. The composition of claim 1 further including a quaternary ammonium conditioning compound in an amount of about 0.1% to about 2.0% by weight of composition.

7. The composition of claim 1, wherein the cysteinamide is included in the composition in an amount of about 9% to about 16% by weight of the composition.

8. A method of breaking sulfur to sulfur bonds in human hair to leave the hair weakened so that it can be reconfigured to a predetermined configuration, while minimizing further damage to damaged hair, including contacting the hair for a predetermined amount of time with an aqueous cysteinamide reducing agentcontaining composition comprising about 1% to about 22% by weight of cysteinamide; and sufficient alkali such that the composition has a pH of about 7.5 to about 9.5; forming the hair in a desired configuration such that the hair is in contact with the reducing agentcontaining composition for a predetermined amount of time while formed in the new configuration; and then removing most of the reducing agent-containing composition from the hair at the expiration of the predetermined time period.

9. The method of claim 8 further including wrapping a plurality of human hair sections around a plurality of mandrels to reconfigure the hair sections in a plurality of curl configurations such that the hair is curl-configured while in contact with the reducing agent-containing composition; and removing the mandrels sequentially after said predetermined time period without testing the hair from one of the first removed mandrels for curl tightness.

10. The method of claim 8, wherein the compositions includes a polyhydric moisturizer in an amount of about 0.1% to about 20% by weight of the composition.

11. The method of claim 10, where the polyhydric moisturizer is selected from the group consisting of polyhydroxyalkyl compounds; polyalkylene glycols; glyceryl ether compounds; ethoxylated fatty alcohols; ethoxylated alkyl phenols; and fatty alcohol polyglycol ether compounds; or mixtures thereof.

12. The method of claim 8, wherein the cysteinamide is included in an amount of about 4% to about 16% by weight of the composition.

13. The method of claim 8, wherein the cysteinamide is included in the composition in an amount of about 9% to about 16% by weight of the composition.

* * * * *